US008586078B2

(12) United States Patent
Faure et al.

(10) Patent No.: US 8,586,078 B2
(45) Date of Patent: Nov. 19, 2013

(54) EMULSION-CONTAINING MEDICAL ARTICLES

(75) Inventors: Marie-Pierre Faure, Ville St. Laurent (CA); Kirill Shingel, Brossard (CA)

(73) Assignee: RBA Pharma Inc., Montreal (CA)

( * ) Notice: Subject to any disclaimer, the term of this patent is extended or adjusted under 35 U.S.C. 154(b) by 912 days.

(21) Appl. No.: 11/633,945

(22) Filed: Dec. 5, 2006

(65) Prior Publication Data

US 2007/0128258 A1 Jun. 7, 2007

Related U.S. Application Data

(60) Provisional application No. 60/742,687, filed on Dec. 5, 2005.

(51) Int. Cl.
*A61L 15/00* (2006.01)
*A61K 9/14* (2006.01)

(52) U.S. Cl.
USPC .......................................... 424/445; 424/488

(58) Field of Classification Search
None
See application file for complete search history.

(56) References Cited

U.S. PATENT DOCUMENTS

| 4,671,954 | A | 6/1987 | Goldberg et al. | 424/450 |
|---|---|---|---|---|
| 4,925,677 | A | 5/1990 | Feijen | 424/484 |
| 4,990,144 | A | 2/1991 | Blott | 604/304 |
| 5,041,292 | A | 8/1991 | Feijen | 424/484 |
| 5,192,535 | A | 3/1993 | Davis et al. | 424/78.04 |
| 5,733,563 | A | 3/1998 | Fortier | 424/422 |
| 5,977,171 | A | 11/1999 | Bowman et al. | 514/530 |
| 6,007,826 | A | 12/1999 | Benita et al. | 424/401 |
| 6,042,815 | A | 3/2000 | Kellner et al. | 424/63 |
| 6,106,855 | A | 8/2000 | Haynes et al. | 424/445 |
| 6,458,386 | B1 | 10/2002 | Schacht et al. | 514/54 |
| 6,632,457 | B1 | 10/2003 | Sawhney | 424/501 |
| 7,125,558 | B2 | 10/2006 | Faure et al. | 424/400 |
| 2003/0149118 | A1* | 8/2003 | Akashe et al. | 516/56 |
| 2004/0082716 | A1 | 4/2004 | Faure et al. | 424/400 |
| 2005/0214376 | A1 | 9/2005 | Faure et al. | 424/488 |
| 2005/0228187 | A1 | 10/2005 | Faure et al. | 558/44 |
| 2006/0222622 | A1 | 10/2006 | Faure | 514/45 |
| 2006/0228416 | A1 | 10/2006 | Faure et al. | 424/448 |

FOREIGN PATENT DOCUMENTS

| EP | 1 280 849 B1 | 8/2006 | C08H 1/00 |
|---|---|---|---|
| WO | WO01/74928 | * 11/2001 | A61K 47/42 |

OTHER PUBLICATIONS

Faraji et al. in Journal of Agricultural an Food Chemistry, 52, 4558-4664, 2004.*
Gayet et al. in Journal of Controlled Release 38 (1996) 177-184.*
OilinWaterEmulsion in www. biology-online.org/dictionary/Emulsion.*
Ramos et al. in Meat Science 64 (2003) 259-263.*
Cardoso et al. in Wound Repair and Regeneration 2004; 12:235-243.*
Cod Liver Oil (http://www.omega3oils.info/codliveroil).*
"Food Today" (www.eufic.org/_article/en/nutrition/fats/artid/The-importance-of-omega-3-and-omega-6-fatty-acids).*
Akay et al., "Microcellular polyHIPE polymer supports osteoblast growth and bone formation in vitro," *Biomaterials*, v. 25, pp. 3991-4000, 2004.
Bokhari et al., "The enhancement of osteoblast growth and differentiation in vitro on a peptide hydrogel-polyHIPE polymer hybrid material," *Biomaterials*, v. 26, pp. 5198-5208, 2005.
Holtze et al., "A Novel Route to Multiphase Polymer Systems Containing Nano-Droplets: Radical Polymerization of Vinylic Monomers in Gelled Water-in-Oil Miniemulsions," *Macromol. Mater. Eng.*, v. 290, pp. 1025-1028, 2005.
Cardoso et al., "Influence of Topical Administration of N-3 and N-6 Essential and N-9 Nonessential Fatty Acids on the Healing of Cutaneous Wounds," *Wound Repair and Regeneration*, v. 12(2), pp. 235-243, 2004.
Dickinson, "Interfacial Interactions and the Stability of Oil-in-water Emulsions," *Pure & Appl. Chem.*, v. 64(11), pp. 1721-1724, 1992.
Hankenson et al., "Omega-3 Fatty Acids Enhance Ligament Fibroblast Collagen Formation in Association with Changes in Interleukin-6 Production," *Proc. Soc. Exp. Biol. Med.*, v. 223, pp. 88-95, 2000.
Kietzmann, "Improvement and Retardation of Wound Healing: Effects of Pharmacological Agents in Laboratory Animal Studies," *Veterinary Dermatology*, v. 10, pp. 83-88, 1999.
Meijer et al., "Particle Size Distribution and Dispersion of Oil-in-water emulsions: An Application of Light Microscopy," *American Laboratory*, pp. 28-31, Apr. 2001.
Seo et al., "Omega-3 Fatty Acids: Molecular Approaches to Optimal Biological Outcomes," *Curr. Opin. Lipidol*, v. 16, pp. 11-18, 2005.
Tcholakova et al., "Interrelation Between Drop Size and Protein Adsorption at Various Emulsification Conditions," *Langmuir*, v. 19, pp. 5640-5649, 2003.

* cited by examiner

*Primary Examiner* — Dennis Heyer
(74) *Attorney, Agent, or Firm* — Roylance, Abrams, Berdo & Goodman, L.L.P.

(57) ABSTRACT

Oil-in-water emulsion gels and medical articles containing an omega-3 oil are disclosed. Also disclosed are methods of preparing and using such emulsion gels and medical articles.

23 Claims, 14 Drawing Sheets a)
b)
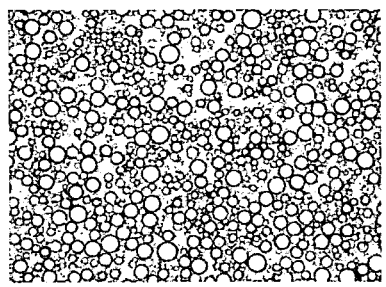
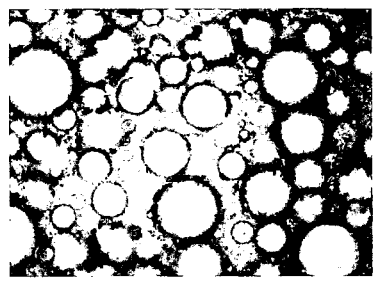
c)
d)
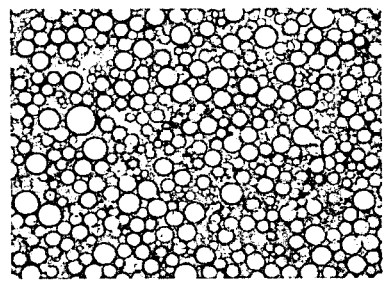
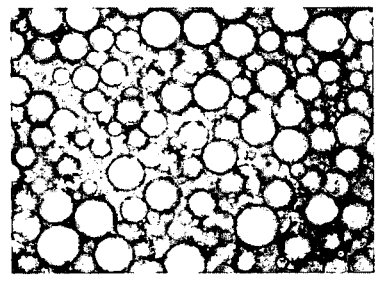
Figures 3a-d

| Wound dressings | Day 10 | Day 16 | Day 20 |
|---|---|---|---|
| Omega-3 oil | 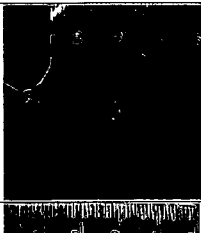 | 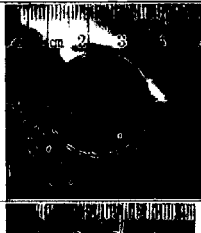 | 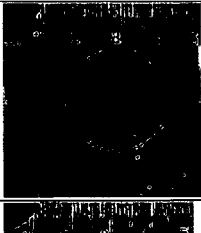 |
| Olive oil |  |  |  |
Figure 8

EMULSION-CONTAINING MEDICAL ARTICLES

This application claims the benefit of the filing date of U.S. Provisional Patent Application Ser. No. 60/742,687, on Dec. 5, 2005, the entire disclosure of which is incorporated by reference herein for all purposes.

FIELD

The present teachings relate to oil-in-water emulsion gels as well as medical articles that include an omega-3 oil. The present teachings also relate to methods of preparing and using such emulsion gels and medical articles.

INTRODUCTION

Emulsions are a class of colloids in which the stable coexistence of two or more immiscible phases is mediated by the presence of emulsifiers. When a surface-active substance is added to, for example, a mixture of oil and water, a monolayer of surfactants is spontaneously formed with their hydrophilic ends facing the water phase and their hydrophobic ends submerged in the oil phase. The formation of the surfactant monolayer decreases the surface tension at the oil-and-water interface and determines the kinetic stability of the system.

An oil-in-water (O/W) emulsion is a particular type of emulsion in which oil droplets are dispersed in water. The size of the oil droplets typically falls in the micron range. The distribution of droplet size is a result of dynamic equilibrium between droplet breakage and interdroplet coalescence. Droplet size can be controlled by various methods including simple shaking, mixing in a rotor/stator mixer, injection and/or filtration through porous membranes, and high-pressure homogenization. The physico-chemical properties of the surfactant used also can affect the efficiency of the emulsification process.

Dissolving a drug in an O/W emulsion can improve the bioavailability of the drug and increase its absorption. In particular, formulating a drug in the form of cream or gel for topical application can largely enhance drug permeation, as the hydrophobic phase of the emulsion provokes structural changes in the lipid layer of the stratum corneum.

However, to stabilize an emulsion, additives such as surfactants are required. When an emulsion is applied to the skin, these surfactants can undesirably penetrate the skin barrier and become systemic substances along with the beneficial agents. As a result, the benefits associated with transcutaneous drug delivery can be offset by the harmful effects these surfactants can cause.

At the same time, while certain emulsion-containing wound dressings are commercially available, these wound dressings are mainly in the form of a mesh gauze impregnated with a petrolatum emulsion. The formulation of other oily substances, including biologically active oily substances, as wound dressings has not been widely studied.

For example, omega-3 polyunsaturated fatty acids (n-3 PUFA) are known to have inflammation-modulating and collagen-stimulating activities. However, while in vitro experiments have shown beneficial effects of omega-3 fatty acids on the growth of epithelial cells (see Ruthig, D. J. (1999), J. NUTR., 129:1791-1798), the results of in vivo studies have been less promising. An in vivo study on the influence of topical administration of n-3 PUFA on the healing of cutaneous wounds in mice, for example, resulted in the observation that such topical treatment did not significantly affect wound closure when compared to control (Ribeiro Barros, C. C. et al. (2004), WOUND REPAIR REGEN., 12:235-243). This finding was in agreement with the results published by Scardino et al., who reported that animals given a diet rich in n-3 PUFA had a delay in total wound closure as a reflection of the decrease in both re-epithelialization and contraction of skin wounds (Scardino, M. E. (1999), VET. DERMATOL., 10:283-290). Such impaired wound closure was explained to be a result of rapid oxidation of n-3 fatty acids in vivo and/or delayed resolution of the inflammatory phase of wound repair.

Accordingly, there is a desire in the art for emulsion-type drug delivery systems and wound treatment methods that can overcome the drawbacks mentioned above and/or provide additional advantages over existing drug delivery systems and wound treatment methods.

SUMMARY

In light of the foregoing, an aspect of the present teachings provides oil-in-water emulsion gels in which emulsifiers are covalently linked to other components in the aqueous phase of the system. The emulsion gels disclosed herein can be formulated to have a semi-solid to solid gel consistency, i.e., not a cream or an ointment. As a result, potentially harmful surfactants can be retained within the solid gel and prevented from absorption through the skin. Drugs can be dissolved in either the hydrophobic phase or the hydrophilic phase, and their delivery is facilitated by the unique structure and composition of the emulsion gels of the present teachings.

Specifically, the emulsion gels of the present teachings include a hydrophobic phase dispersed within a hydrogel matrix, which is made of one or more proteins covalently crosslinked by one or more hydrophilic, gel-forming polymers. In other words, the emulsion gels include a continuous hydrophilic phase and a dispersed hydrophobic phase. The hydrogel matrix can include proteins such as bovine serum albumin, human serum albumin, lactalbumin, ovalbumin, soy albumin, pea albumin, hydrolyzed soy protein, hydrolyzed wheat protein, casein, and their mixtures. In particular embodiments, the hydrogel matrix can include proteins that are water-soluble and/or have antioxidant properties. Polymers that can be used to crosslink the water-soluble proteins include polyethylene glycol and its derivatives.

The hydrophobic phase dispersed within the hydrogel matrix can include a natural oil. For example, various animal oils, vegetable oils, and mineral oils can be used singly or in combination. In particular embodiments, oils containing a high level of omega-3 fatty acids, e.g., alpha-linolenic acid, eicosapentaenoic acid, and docosahexaenoic acid, can be used. Examples of oils containing a high level of omega-3 fatty acids include, but are not limited to, flaxseed oil, walnut oil, and oils from fatty fish and marine planktons. The hydrophobic phase can include a biologically active agent.

In another aspect, the present teachings provide a method for preparing the oil-in-water emulsion gels described above. The method generally can include dispersing an oil in an aqueous protein solution to form an oil-in-water emulsion, and adding a hydrophilic, gel-forming polymer to crosslink covalently a protein in the oil-in-water emulsion to form an emulsion gel. The method can further include dissolving a biologically active agent in the oil before forming the oil-in-water emulsion.

The emulsion gels described above are generally water-insoluble. Due to the hydrophilic nature of the protein and the gel-forming polymer, emulsion gels of the present teachings can be highly swellable, and are typically swollen with water or other aqueous media prior to use. Additionally, the emulsion gels can be processed by extrusion, injection-molding, or casting into various predetermined shapes and dimensions. For example, the emulsion gels disclosed herein can be formed into a film. In some embodiments, a backing can be attached to a surface of the emulsion gel as a support layer. The emulsion gels of the present teachings possess excellent mechanical and optical properties, and can be used as drug delivery devices or other medical articles including but not limited to wound dressing applications. For example, the emulsion gels of the present teachings can be applied topically for the treatment of burns, acute wounds, chronic wounds, necrotic wounds, skin lacerations, or skin irritation.

A further aspect of the present teachings provide medical articles that include an omega-3 oil. Such medical articles can be applied topically, for example, as wound dressings to promote healing of different types of wounds and reduce or eliminate scar formation, or as cosmetic patches to improve general skin conditions. The medical article can include a polymeric film and/or a fabric layer. In some embodiments, the medical article can include a polymeric matrix or a polymeric binder, and the omega-3 oil can be dispersed within the polymeric matrix, or otherwise incorporated into the polymeric film using a polymeric binder. In particular embodiments, the polymeric matrix can be a hydrogel matrix that includes a protein covalently crosslinked by a hydrophilic, gel-forming polymer. In some embodiments, the medical article can include a fabric layer impregnated with omega-3 oil.

The foregoing, and other features and advantages of the present teachings, will be more fully understood from the following figures, description, and claims.

BRIEF DESCRIPTION OF FIGURES

This patent or application contains at least one drawing executed in color. Copies of this patent or patent application publication with color drawing(s) will be provided by the United States Patent and Trademark Office upon request and payment of the necessary fee.

A skilled artisan will understand that the drawings described below are for illustration purposes only and are not necessarily to scale. The drawings are not intended to limit the scope of the present teachings in any way.

FIGS. 3a-d show microscopic images of certain embodiments of an emulsion gel according to the present teachings prepared with different oil-to-water ratios.

FIG. 8 presents representative color photographs of a first full-thickness wound treated with wound dressings according to the present teachings and a second full-thickness wound treated with comparative wound dressings, on Day 10, Day 16, and Day 20, of a 30-day study period. The black circle shows the size of the initial wounds created on Day 0.

DETAILED DESCRIPTION

Figure 1:
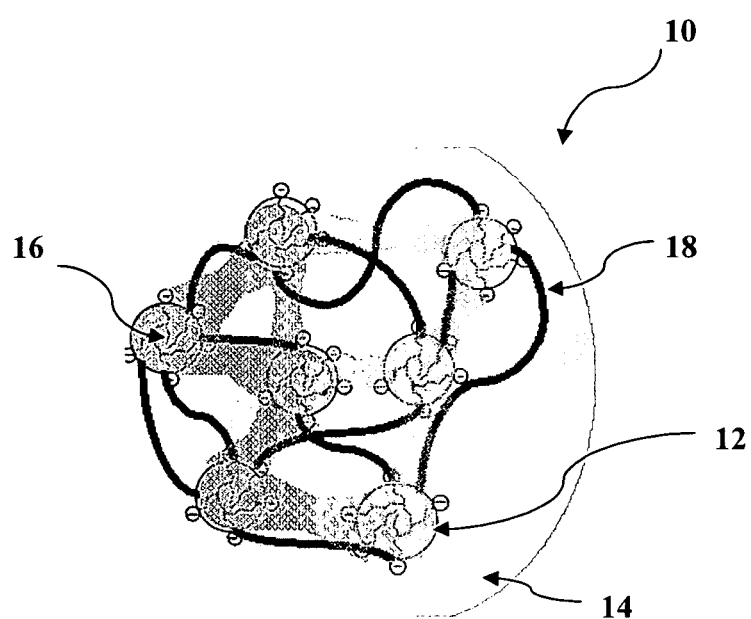
FIG. 1 is a schematic representation of a possible structure of an embodiment of an emulsion gel according to the present teachings.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

An aspect of the present teachings provide a family of solid emulsion gels with hydrophilic properties. Specifically, the solid emulsion gels are oil-in-water emulsion gels that include a hydrophobic phase dispersed within a hydrogel matrix (i.e., the continuous phase is the hydrogel matrix and the dispersed phase is hydrophobic). The hydrogel matrix is composed of a protein covalently crosslinked by a hydrophilic, gel-forming polymer. Generally, an emulsion gel of the present teachings can be prepared by combining the protein in solution with the hydrophobic phase under high shear, and then adding the hydrophilic, gel-forming polymer to the emulsion to form the emulsion gel.

Proteins have long been known as an efficient naturally-occurring emulsifier, and in this case, the hydrophobic regions of the protein can help to stabilize the dispersion of the hydrophobic phase in the protein solution. The hydrophilic, gel-forming polymer acts as a crosslinking agent and connects the hydrophilic moieties of the protein molecules to form a stable three-dimensional network. The resulting emulsion gel has a solid consistency and can undergo rapid swelling without discernible dissolution. The dispersed hydrophobic phase enables transport of hydrophobic drugs while the continuous hydrophilic phase retains various desirable properties of a hydrogel.

Suitable proteins include albumins derived from various sources. Examples include bovine serum albumin, human serum albumin, lactalbumin, ovalbumin, soy albumin, wheat albumin, pea albumin, and albumins from marine sources (e.g., fish protein or algae). Other suitable proteins include hydrolyzed soy protein, hydrolyzed wheat protein, casein, and gelatin. While naturally-derived proteins can be used, modified proteins including, but not limited to, modified soy proteins and soy polymers (e.g. Arcon® modified soy proteins available from Archer Daniel Midlands, Decatur, Ill. and Pro-Cote® soy polymers available from Dupont Protein Technologies, St. Louis, Mo.) also can be used to prepare emulsion gels of the present teachings. In addition, mixtures of any of the above-mentioned proteins also can be used. The protein is preferably water-soluble at room temperature. For example, the protein can have a solubility of at least 50 mg/mL in water at room temperature, a solubility of at least 100 mg/mL in water at room temperature, a solubility of at least 500 mg/mL in water at room temperature, or a solubility of at least 1000 mg/mL in water at room temperature.

In some embodiments, the protein can have antioxidant properties. Recent studies suggest that many proteins, particularly soy proteins, can inhibit lipid oxidation when they expose a positive charge at the water-oil interface. This antioxidant effect was found to be associated with the presence of a large proportion of free sulfhydryl groups in the soy protein structure. See Faraji, H. et al. (2004), *J. Aggr. Food Chem.*, 52: 4558-4564. Faraji et al. showed that a continuous phase of proteins protected omega-3 fatty acids from oxidative degradation. In addition to the content of sulfhydryl groups in the protein molecules, other factors including solubility, degree of denaturation, and lipid-to-protein ratio have also been shown to play important roles in the emulsion-stabilizing effect of a protein structure. See Tcholakova, S. et al. (2003), *Langmuir*, 19: 5640-5649; Wong, P. Y. Y. et al. (2003), *J. Dairy Sci.*, 86: 746-754; and Hogan, S. et al. (2001), *J. Aggr. Food Chem.*, 49:1934-1938.

In certain embodiments, in place of or in addition to the protein, a polymer containing amine groups, particularly a polymer having pendant groups that are primary amines, can be used to stabilize the emulsion. For example, polyallyl amines (e.g., poly(allylamine hydrochloride)) or chitosan can be used for this purpose.

Various hydrophobic substances can be combined with the protein solution to form the initial emulsion. Any of a variety of pharmacologically acceptable oils or organic solvents can be used. The term "pharmacologically acceptable" refers to molecular entities and compositions that do not produce an adverse, allergic or other untoward reaction when administered to a mammal, such as a human. Pharmacologically acceptable organic solvents include, but are not limited to, water-immiscible alcohols such as propanol, hexanol and the like; substituted heterocyclic compounds such as N-methyl-2-pyrrolidone (NMP) and 2 pyrrolidone and the like; esters of carbonic acid and alkyl alcohols such as propylene carbonate and the like; esters of mono-, di-, and tricarboxylic acids such as ethyl lactate and the like; ketones such as acetone and the like; dialkylamides such as dimethylsulfoxide (DMSO) and the like; and mixtures and combinations thereof.

In certain embodiments, a natural oil is used. For example, various animal oils, vegetable oils, and mineral oils can be used singly or in combination. Examples include, but are not limited to, arachis oil, castor oil, coconut oil, corn oil, sesame seed oil, rapeseed oil, sunflower oil, flaxseed oil, walnut oil, fish oils, oils from marine planktons, and mixtures thereof. Oils containing a high level of omega-3 fatty acids (e.g., alpha-linolenic acid, eicosapentaenoic acid, and docosahexaenoic acid) are especially preferred. Examples of omega-3-rich oils ("omega-3 oils") include flaxseed oil, walnut oil, and oils from fatty fish and marine planktons.

The initial emulsion according to the present teachings can comprise from 1% to 50% by weight of the hydrophobic substance, from 0.5% to 25% by weight of the water-soluble protein, and from 25% to 98.5% by weight of water. The emulsion can be prepared by homogenizing the hydrophobic substance and the protein solution at high shear to produce microdroplets of the hydrophobic phase dispersed in the aqueous protein solution. Typically, the droplets have a maximum dimension less than 25 µm, for example, in the range of 0.5 µm to 10 µm.

Homogenization can be carried out by any suitable means, such as by a jet homogenizer, ultrasonic homogenizer or blade/shear homogenizer. Other mixers such as rotor/stator mixers and vortex mixers can be used to thoroughly mix and disperse the hydrophobic substance in the aqueous protein solution. In some embodiments, the resultant emulsion is stable over a period of at least 6 hours without visual phase separation.

Biologically active agents, either singly or in combination, can be included in the hydrophobic phase and/or the hydrogel matrix. As used herein, the term "biologically active agent" refers to medicaments, drugs, or other suitable biologically, physiologically, or pharmaceutically active substances that are capable of providing local or systemic biological, physiological, or therapeutic effect in the body of a mammal. A biologically active agent typically is released from the emulsion gel across the skin barrier and/or into adjacent or surrounding tissue fluids. Examples of biologically active agents can include antiallergic agents, antimicrobial agents, analgesic agents, antiphlogistics, anti-itch agents, antibiotics, healing agents, astringents, anesthetics, and the like.

Hydrophobic biologically active agents can include certain steroids such as budesonide, testosterone, progesterone, estrogen, flunisolide, triamcinolone, beclomethasone, betamethasone; dexamethasone, fluticasone, methylprednisolone, prednisone, hydrocortisone, and the like; certain peptides such as cyclosporin cyclic peptide and retinoids such as all-cis retinoic acid, 13-trans retinoic acid, and other vitamin A and beta carotene derivatives; vitamins D, E, and K and water insoluble precursors and derivatives thereof; prostagladins and leukotrienes and their activators and inhibitors including prostacyclin (epoprostanol), and prostaglandins $E_1$ $E_2$; tetrahydrocannabinol; lung surfactant lipids; lipid soluble antioxidants; hydrophobic antibiotics and chemotherapeutic drugs such as amphotericin B and adriamycin and the like. A hydrophobic biologically active agent can be dissolved in the hydrophobic phase before emulsification.

In some embodiments, the one or more pharmacologically acceptable oils or organic solvents of the hydrophobic phase can be themselves biologically active. For example, the therapeutic effect of omega-3 rich oil has been widely studied and reported (see e.g., Seo, T. et al. (2005), *Curr. Opin. Lipidol.,* 16: 11-18).

Hydrophilic biologically active agents can include various known biologically active agents formulated as a salt. Examples can include lidocaine HCl, dopamine HCl, ephedrine sulfate, penicillin G sodium and the like. Water-soluble polypeptides and oligopeptides such as various cytokines and growth factors also can be used. A hydrophilic biologically active agent can be integrated into the hydrogel matrix after the emulsion gel is formed by swelling the emulsion gel in an integration solution containing the hydrophilic biologically active agent. Hydrophilic biologically active agents, however, can be included into the hydrophilic phase before or after emulsification and/or polymerization.

Following the formation of the protein-stabilized emulsion, a hydrophilic, gel-forming polymer can be added to the emulsion to form an emulsion gel. Suitable polymers can include biocompatible polymers such as poly(alkylene oxide), poly(vinyl pyrrolidone), polyacrylamide, and poly(vinyl alcohol). As used herein, the term "biocompatible polymer" is understood to mean any polymer that does not appreciably alter or affect in any adverse way the biological system into which it is introduced. Polyethylene oxides, such as polyethylene glycols (PEG) having weight average molecular weights from about $0.05 \times 10^4$ Daltons to about $10 \times 10^4$ Daltons, can be particularly useful. In particular embodiments, PEGs having weight average molecular weights from about 0.2 to about $3.5 \times 10^4$ Daltons, or about 8,000 Daltons, can be employed.

The hydrophilic, gel-forming polymer can act as a crosslinking agent that connects the hydrophilic regions of the water-soluble proteins together to form a three-dimensional network. In some cases, it can be necessary to convert the end-groups of the polymer into more reactive functional groups to effect covalent crosslinking of the protein. For example, in embodiments where PEG is used, one or both of the hydroxyl end-groups can be converted into a functional group that is capable of reacting with the various chemical groups (e.g., amino, thiol, carboxyl, and carboxylic groups) commonly found in proteins, i.e., the PEG can be derivatized.

In some embodiments, a non-polymeric crosslinking agent can be used to crosslink the water-soluble protein. Suitable crosslinking agents can include a wide variety of homo- and hetero-bifunctional agents. Examples can include, but are not limited to, gluteraldehyde, ethylene glycol diglycidyl ether, epoxides, and furfural (see e.g., Wang, N. et al. (2004), *J. Appl. Polym. Sci,* 95: 465-473; Swain, S. N. et al. (2004), *J. Appl. Polym. Sci.,* 93: 2590-2596).

Several chemical procedures have been developed for the preparation of functionalized (activated) PEGs (also referred to herein as "derivatized PEGs"). These functionalized/activated PEGs can then be used to react with free amino groups of proteins. For example, PEGs have been successfully activated by reaction with 1,1-carbonyl-di-imidazole, cyanuric chloride, tresyl chloride, 2,4,5-trichlorophenyl chloroformate or p-nitrophenyl chloroformate, various N-hydroxy-succinimide derivatives, by the Moffatt-Swern reaction, as well as with various diisocyanate derivatives (see e.g., Zalipsky S. (1995), *Bioconjugate Chem.,* 6: 150-165 and references therein; Beauchamp, C. et al. (1983), *Anal. Biochem.,* 131: 25-33; Nashimura, H. et al. (1983), *Life Sci.,* 33: 1467-1173; Delgado, C. et al. (1990), *Appl. Biochem.,* 12: 119-128; Wirth, P. et al. (1991), *Bioorg. Chem.,* 19: 133-142; Veronese, F. M. et al. (1985), *Biochem. Biotech.,* 11: 141-152; Sartore et al. (1991), *Biochem. Biotechnol.,* 27: 45; Anderson, W. L. et al. (1988), *J. Immunol. Methods,* 109: 37-42; Zalipsky, S. et al. (1990), *J. Bioact. Compat. Polym.,* 5: 227-231; and U.S. Pat. No. 6,773,703).

The derivatization/activation of PEGs with p-nitrophenyl chloroformate to generate PEG-dinitrophenyl carbonates has been described in U.S. Pat. No. 5,733,563 and by Fortier and Laliberte (Fortier et al. (1993) BIOTECH. APPL. BIOCHEM. 17: 115-130). This reaction usually is carried out in acetonitrile containing triethylamine (TEA) over a period of about 5 hours at 60° C.

U.S. Patent Application Publication No. 2005/0080206 and U.S. patent application Ser. No. 11/071,877 describe alternative methods for preparing activated PEGs with p-nitrophenyl chloroformate. The method described in U.S. Patent Application Publication No. 2005/0080206 involves a reaction carried out at room temperature using an aprotic solvent, such as methylene chloride ($CH_2Cl_2$), in the presence of a catalyst, such as dimethylaminopyridine (DMAP). U.S. patent application Ser. No. 11/071,877 describes a method of activating PEG by reacting molten PEG with an activator in a solvent-free environment.

The activated PEG can be dissolved in water and added to the kinetically stable but thermodynamically unstable emulsion. The crosslinking reaction can be performed under basic conditions and without the use of a buffer as described in European Publication No. EP 0 705 298. For example, the protein emulsion can be prepared in a strong base (e.g. sodium hydroxide). In some embodiments, an equal (1:1) volume of the activated PEG solution and the protein solution can be used to prepare the protein emulsion.

The crosslinking reaction between the protein and the polymer can confer a semisolid to solid consistency to the resulting emulsion gel. The resulting emulsion gel can include a hydrophobic phase dispersed in a hydrogel matrix. Depending on the amount of hydrophobic substances in the system, the hydrophobic phase can be uniformly and quasi-continuously dispersed within the continuous hydrogel matrix. The droplet size of the hydrophobic phase also can approach unimodal.

The emulsion gel product can be processed into various shapes (e.g. films, discs, blocks, pellets, pastilles, fibers, etc.) and sizes. For example, the emulsion gel can be placed between two pieces of glass to achieve a certain thickness. Other processing techniques include extrusion, casting, injection-molding, pelleting, pastilling, and shredding. One or more support layers also can be attached to the final emulsion gel. For example, a polymeric backing can be attached to the emulsion gel with or without the use of an adhesive. A possible method is described in U.S. Patent Application Publication No. 2004/0082716, in which the surface of a polymeric backing is exposed to an activated gas to make it adhesive to a surface of a hydrogel. More specifically, a polymeric backing, such as polyethylene terephthalate, can be exposed to plasma of various gases or mixture of gases, including, but not limited to, nitrogen, ammonia, oxygen, hydrogen, and various noble gases, produced by an excitation source such as microwave and radiofrequency.

The emulsion gel can include a buffer system to help control the pH, to prevent discoloration and/or breakdown due to hydrolysis. Suitable buffers can include, but are not limited to, sodium potassium tartarate and/or sodium phosphate monobasic, both of which are commercially available from Sigma-Aldrich Chemical Co. (Milwaukee, Wis.). In certain embodiments, the emulsion gel can be loaded with a buffer solution to adjust the pH of the emulsion gel within the range of 3.0-9.0. In some embodiments, an acid or a base can be used instead of the buffer solution for the same purpose. The use of a buffer system can provide the emulsion gels with a commercially acceptable shelf-life. Antioxidants can be included to prevent oxidative degradation of the hydrophobic phase. Examples of antioxidants can include, but are not limited to, vitamin A and eugenol.

The hydrophobic phase of the emulsion gel can be exchanged with another organic solvent by means of solvent exchange. Emulsion gels of the present teachings can be incubated in an organic solvent in which the hydrophobic phase of the emulsion gels is known to be soluble. Incubation of the emulsion gels in such a solvent can lead to the complete replacement of the hydrophobic phase of the emulsion gels with the solvent. The solvent can then be evaporated, and the resultant material can be subsequently integrated with another oil as the hydrophobic phase of the emulsion gels. Alternatively, the solvent can be exchanged by incubating the emulsion gels in a desirable oil. Suitable solvents for such solvent exchange can include the various organic solvents described above.

To ensure that the emulsion gels are aseptic, the emulsion gels can be prepared in a clean room. Additionally, preservatives and antimicrobial agents can be incorporated either singly or in combination into the emulsion gels. A preservative having antimicrobial properties sold under the name of LIQUID GERMALL® PLUS (International Specialty Products, Wayne, N.J.) for example, can be used. The preservative LIQUID GERMALL® PLUS has been incorporated into cosmetic products and contains propylene glycol (60 wt. %), diazolidinyl urea (39.6 wt. %), and iodopropynyl butylcarbamate (0.4 wt. %). Other additives, including colorants, fragrance, binders, plasticizers, stabilizers, fire retardants, cosmetics, and moisturizers, can also be present. These additives can be incorporated into the hydrophobic phase before emulsification, or into the hydrophilic phase before or after emulsification and/or polymerization. It is envisaged that the emulsion gels according to the present teachings will preferably be substantially free from added emulsifiers other than the protein and hydrophilic polymer used to form the emulsion gel. However, in some cases, it can be advantageous to include added emulsifiers such as lecithins, mono- and diglycerides of fatty acids and sorbitan esters.

The emulsion gels of the present teachings can have useful physiological, mechanical, and optical properties—including, for example, one or more of a near zero irritation index, a low sensitization potential, high water content, hydrophilicity, oxygen-permeability, viscoelasticity, moderate self-adhesiveness, translucidity, and capability for controlled release of both hydrophilic and hydrophobic drugs. These properties, individually and in combination, make these emulsion gels suitable for various pharmaceutical, medical, and cosmeceutical applications. Additionally, the plasticity and/or elasticity of the emulsion gels can be modified for different applications by varying the amounts of the polymer and the protein used, the molecular weight of the polymer used, and/or the type of the protein used.

The emulsion gels according to the present teachings can be particularly useful as wound dressings and drug delivery devices. As wound dressings, the emulsion gels can be applied to treat various types of wounds, particularly burns, acute wounds, chronic wounds, necrotic wounds, skin lacerations, and infected wounds. A drug delivery device including the emulsion gel of the present teachings can be used in topical, systemic, intratumoral, subcutaneous, and rectal applications, and particularly, in transdermic applications. The emulsion gels according to the present teachings can be applied to open or intact skin to modulate topical inflammatory response, including inflammation caused by various skin disorders (e.g., dermatitis).

FIG. 1 is a schematic representation of a possible structure of an embodiment of an emulsion gel according to the present teachings. As shown, an emulsion gel 10 includes droplets of a hydrophobic substance 12 dispersed in a continuous hydrophilic phase 14 stabilized by proteins 16. The proteins are in turn crosslinked by a hydrophilic, gel-forming polymer 18. The result is a stable solid reticulated emulsion gel.

Figure 2:
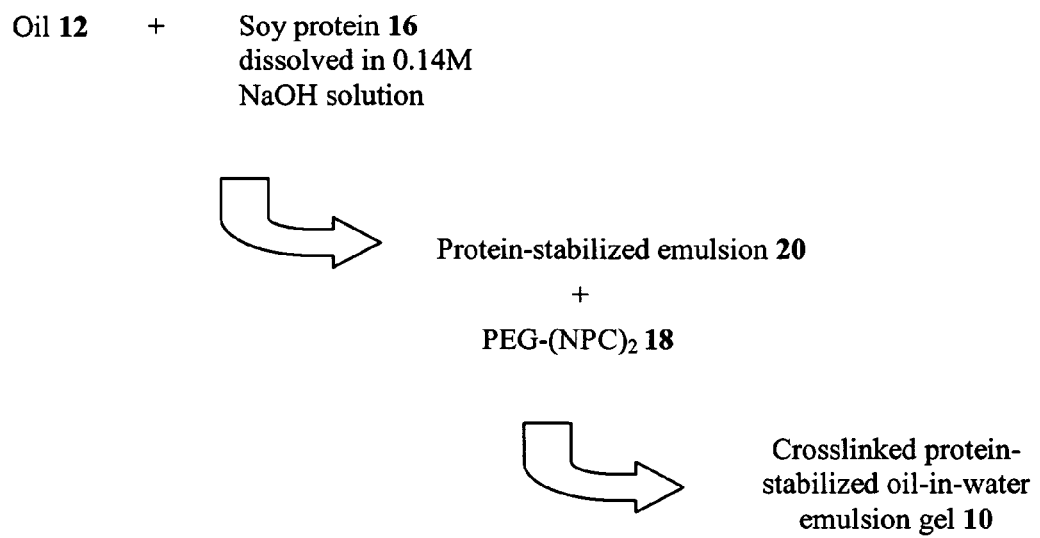
FIG. 2 illustrates a method of preparing an embodiment of an emulsion gel according to the present teachings.

FIG. 2 illustrates a method of preparing an embodiment of an emulsion gel according to the present teachings. A protein 16 (e.g., soy protein) is dissolved in a 0.14 M NaOH solution to form an aqueous protein solution. Subsequently, a hydrophobic substance 12 (e.g., an oil), which optionally can include a hydrophobic drug dissolved therein, is dispersed in the aqueous protein solution to form an oil-in-water emulsion 20. Finally, a hydrophilic, gel-forming polymer 18 (e.g., dinitrophenyl carbonyl polyethylene glycol (PEG-$(NPC)_2$) is added to covalently crosslink the protein in the oil-in-water emulsion to form an emulsion gel 10.

A further aspect of the present teachings provide medical articles that include an omega-3 oil. Such medical articles can be applied topically, for example, as wound dressings to promote healing of different types of wounds and reduce or eliminate scar formation, or as cosmetic patches to improve general skin conditions. In some embodiments, the medical article can be a hydrocolloid-based wound dressing (e.g., a matrix that includes cellulose and optionally other gel-forming agents such as, but not limited to, gelatin, pectic, etc.), an alginate-based wound dressing (e.g., calcium alginates, sodium alginates, etc.), a foam-based wound dressing (e.g., urethane foam dressing, polyvinyl alcohol foam dressing etc.), a hydrogel-based wound dressing (e.g., a water-swellable polymeric matrix), or a fiber-based wound dressing (e.g., dry gauze or keratin-based wound dressing). In certain embodiments, the medical article can include one or more types of wound dressings. For example, the medical article can include a primary dressing (e.g., a hydrogel-based wound dressing) and a secondary dressing (e.g., a foam-based wound dressing).

In some embodiments, the omega-3 oil can be incorporated into a polymeric film that forms the medical article in whole or in part. For example, the omega-3 oil can be dispersed within a polymeric matrix. Alternatively, the omega-3 oil can be incorporated using a polymeric binder. In particular embodiments, the omega-3 oil can be dispersed within a continuous hydrogel matrix that includes a protein covalently crosslinked by a hydrophilic, gel-forming polymer. In other embodiments, the medical article can include a fabric layer impregnated with omega-3 oil.

The emulsion gels and the medical articles of the present teachings can be used in wound care management and can offer desirable properties including but not limited to one or more of the following: anti-inflammatory activity, anti-bacterial activity, the maintenance of a moist environment, water-permeability, easy application, ability to conform to anatomical contours, non-toxicity, non-allergenicity, ability to accelerate wound closure, and ability to prevent scar formation.

The following examples are provided to illustrate further and to facilitate the understanding of the present teachings and are not intended to limit the scope of the present teachings.

Example 1

Synthesis of Solid Emulsion Gels

Soy protein isolate (SPI) with a protein content of 96% was used as received from Archer Daniels Midland Co. (Decatur, Ill.). The protein was acid hydrolyzed in a 10% HCl solution at 80° C. for 4 hours, followed by purification steps. The purification steps involve neutralization of the protein solution and ultrafiltration of the protein colloidal solution using a membrane with a cut-off limit of 10 kDa. The solution of hydrolyzed and purified soy protein was then dehydrated by either freeze-drying or spray-drying techniques. The purified hydrolyzed soy protein was added into a 0.14 M NaOH solution to give a concentration of 120 mg/mL.

A series of protein-stabilized emulsions were then prepared by thoroughly mixing the protein solution provided above with an oleaginous component (e.g., omega-3 oil, mineral oil, and a 50/50 mixture of omega-3 oil and mineral oil). The volume ratio of the protein solution to the oil ranged from 1.0/0.2 to 1.0/2.0. The resultant emulsions were stable over a period of 12 hours without visual phase separation. In some of the samples, capsaicin from Sigma-Aldrich Chemical Co. (Milwaukee, Wis.) was dissolved in the oil phase of the emulsions (0.025% in the final formulation) before emulsification with the hydrolyzed soy protein.

One volume of an aqueous solution of dinitrophenyl carbonyl polyethylene glycol (PEG-(NPC)$_2$) was mixed with one volume of the protein emulsion obtained above. The resultant mixture was placed between two pieces of glass to obtain a gel with a thickness of about 1.8 mm or 1.0 mm.

The emulsion gels prepared according to the procedure described above were found to have a rubbery feel and were easy to handle. Without wishing to be bound to any particular theory, it is believed that the matrix reticulation observed is due to the formation of urethane linkages between free amino groups of the protein and the PEG-carbonate moieties. After polymerization was complete, the gel was placed into phosphate buffer saline (PBS) to wash out p-nitrophenol (pNP) that was formed as a by-product of the crosslinking reaction.

Light microscopy technique was used to characterize the structures of the emulsion gels obtained. Thin film samples of emulsion gels synthesized using different oil-to-water ratio were cast between microscope slides. Microscopic images of the gel samples were obtained using a Leica DFC Camera Microscope.

Emulsion gels prepared with protein(aq.):PEG:oil ratios of 1.0:1.0:0.2 and 1.0:1.0:1.0 were observed to have irregularly-shaped oil droplets. In these systems, the water phase was found to be dominant, and the size distribution of the oil droplets was rather broad and multimodal. Droplets were mostly isolated, although regions of coalesced droplets were also observed.

Emulsion gels prepared with a protein(aq.):PEG:oil ratio of 1.0:1.0:2.0 showed a largely improved emulsion system. Here, two volumes of aqueous solutions (one of PEG and one of protein) were combined with 2.5 volumes of omega-3 oil. Small spherical droplets of oil were observed to occupy the volume uniformly, with size distribution being almost unimodal.

Additionally, it was observed that using mineral oil in combination with omega-3 oil as the oleaginous component resulted in increased stability of the protein-oil emulsion and improved mechanical properties of the system.

FIGS. 3a-d show microscopic images of emulsion gel samples prepared with different oil-to-water ratios. FIGS. 3a and 3b are 20× and 40× magnification images of an emulsion gel sample prepared with 33% of oil (by volume). FIGS. 3c and 3d are 20× and 40× magnification images of an emulsion gel sample prepared with 50% of oil (by volume).

Example 2

Swelling Behavior of Solid Emulsion Gels

The co-existence of two immiscible liquids in a single compartment was expected to affect the swelling and diffusion behavior, as well as the mechanical properties of the system. To verify the correlation between the component composition of the material and its swelling properties in aqueous environments, emulsion gel samples containing 0-50 vol. % of oil were prepared and studied in terms of their swelling behavior and affinity towards water.

Following synthesis according to the procedures described in Example 1, samples containing different amounts of oil were cut into round pieces with a diameter of approximately 2.5 cm. These samples were immersed in PBS solution to wash out pNP and to let the material attain equilibrium water content. After 6-12 hours of incubation, the samples were measured again, and the ratio between their initial dimension and their final dimension was considered the expansion factor.

To estimate the component composition of the gel at equilibrium, the following theoretical considerations were employed. The initial composition of the emulsion gel was expected to change upon swelling due to absorbance of extra water, which would lead to a decrease in the percentage of the oil phase. Because the oil phase was integrated into the matrix, oil was not expected to be released from the material. Therefore, any increase in the linear dimensions of the samples should correlate directly with the expansion degree. Based on the values of the expansion factor, the percentage of each component can be calculated.

Specifically, the initial volume percentage of each component can be calculated as follows:

$$\text{Oil, \%} = \frac{\text{Oil, mL}}{\text{Protein, mL} + \text{PEG, mL} + \text{Oil, mL}} \cdot 100\% \quad (1)$$

$$\text{Water, \%} = \frac{1.66 \cdot \text{Oil, \%} \cdot \text{Protein, mL}}{\text{Oil, mL}} \quad (2)$$

$$\text{Protein, \%} = \frac{0.12 \cdot \text{Oil, \%} \cdot \text{Protein, mL}}{\text{Oil, mL}} \quad (3)$$

$$\text{PEG, \%} = \frac{0.22 \cdot \text{Oil, \%} \cdot \text{PEG, mL}}{\text{Oil, mL}} \quad (4)$$

In Equations 1-4 above, the variables [Oil, %], [Oil, mL], [Water, %], [Protein, %], and [PEG, %] refer to, respectively, the volume percentage of the oil phase, the volume of oil used to prepare the initial emulsion, the volume percentage of water, and the volume percentages of protein and PEG in the structure.

Based on the amount of the individual components used initially for synthesis, the initial composition of the solid emulsion gel material was calculated using equations 1-4. Table 1 summarizes the results.

TABLE 1

Initial composition of emulsion gel samples.

| Soy:Oil:water | Soy (%) | PEG (%) | Oil (%) | Water (%) |
|---|---|---|---|---|
| 10:2:10 | 5.46 | 10.01 | 9.1 | 75.5 |
| 10:5:10 | 4.80 | 8.82 | 20.0 | 66.4 |
| 10:10:10 | 3.96 | 7.26 | 33.3 | 55.3 |
| 10:15:10 | 3.42 | 6.27 | 42.8 | 47.4 |
| 10:20:10 | 3.00 | 5.50 | 50.0 | 41.5 |

After swelling, the initial linear dimension and the final linear dimension of the emulsion gel samples were measured. The ratio between the final linear dimension and the initial linear dimension is herein referred to as the expansion factor $f_{EXP}$. The expansion factor is plotted against the initial oil content of the samples in FIG. 4.

Figure 4:
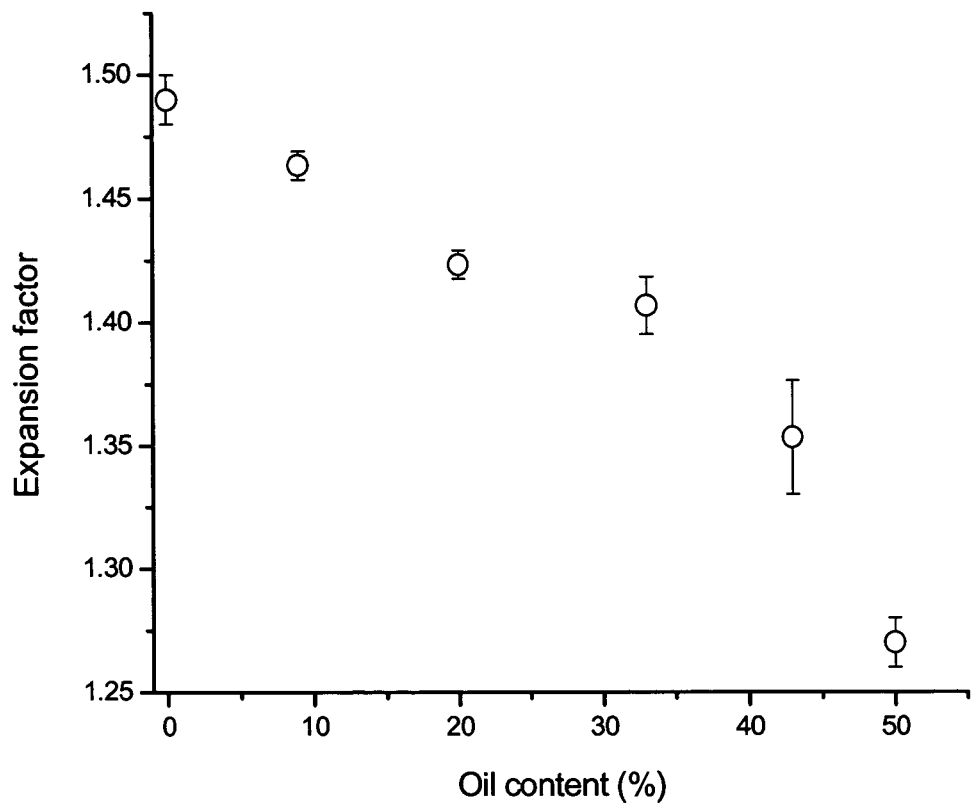
FIG. 4 is a graphical representation of the correlation between the initial oil content of certain embodiments of an emulsion gel according to the present teachings and their expansion factor. The expansion factor refers to the degree of expansion in the linear dimension of an emulsion gel after being swollen in water to attain its equilibrium water content.

As shown in FIG. 4, for samples with an initial oil content between 0 and 50% (by volume), the $f_{EXP}$ value ranges from 1.50 to 1.25, respectively. It can be seen that the expansion of the gel due to swelling was much more pronounced for samples with low oil content. It appears that the swelling capacity of the emulsion gel, expressed in terms of the expansion factor, decreases with an increase in the initial oil content.

To correlate the swelling behavior data with estimated values of the final component composition of the gel samples after equilibrium swelling, the final component composition of the swollen gel samples was determined according to equations 5-8 below:

$$Oil_{FINAL}, \% = \frac{Oil_{INITIAL}, \%}{f_{EXP}} \quad (5)$$

$$Protein_{FINAL}, \% = \frac{Protein_{INITIAL}, \%}{f_{EXP}} \quad (6)$$

$$PEG_{FINAL}, \% = \frac{PEG_{INITIAL}, \%}{f_{EXP}} \quad (7)$$

$$Water_{FINAL}, \% = 100 - (Oil_{FINAL}, \% + Protein_{FINAL}, \% + PEG_{FINAL}, \%) \quad (8)$$

Table 2 shows the component composition of the different gel samples after swelling in aqueous solutions.

TABLE 2

Composition of emulsion gel samples at equilibrium swelling capacity in aqueous environment. The values are mean values (n = 8).

| Soy:Oil:water | Soy (%) | PEG (%) | Oil (%) | Water (%) |
|---|---|---|---|---|
| 10:2:10 | 3.74 | 6.86 | 6.2 | 83.2 |
| 10:5:10 | 4.80 | 8.82 | 14.2 | 66.4 |
| 10:10:10 | 3.99 | 7.33 | 23.6 | 55.3 |
| 10:15:10 | 3.42 | 6.27 | 31.7 | 47.4 |
| 10:20:10 | 3.00 | 5.50 | 39.4 | 41.5 |

Figure 5:
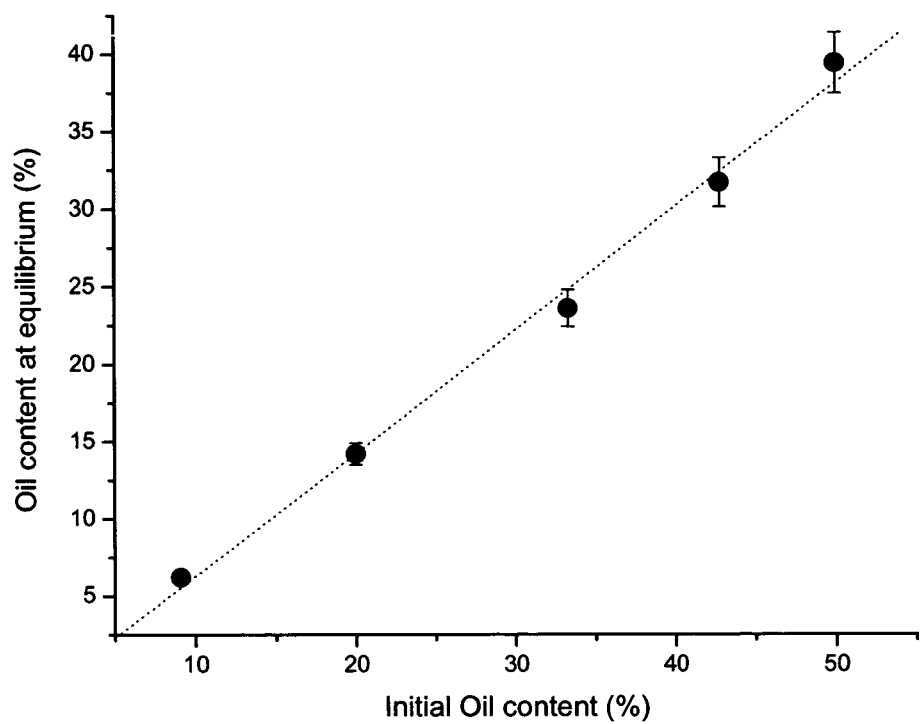
FIG. 5 is a graphical representation of the correlation between the initial oil content and the final oil content of certain embodiments of an emulsion gel according to the present teachings in terms of volume percentage.

Since the swelling capacity of the emulsion gel appears to depend on the initial oil content, it was of interest to study how swelling of the material alters the oil content. FIG. 5 shows the correlation between the initial oil content and the final oil content of the samples in terms of volume percentage. It can be seen that the final oil content is proportional to the initial oil content in the studied materials.

The linearity in the correlation between the initial oil content and the final oil content is illustrative of the fact that the oil content in the emulsion gel samples changes predictably according to the initial volume of the oil phase in the emulsion gel samples. As shown in FIG. 5, the correlation between the final oil content, $Q_{FIN}$, and the initial oil content, $Q_0$, can be described by the following equation:

$$Q_{FIN} = XQ_0 \quad (9)$$

For the particular series of samples studied here, X was found to be 0.752 ($R^2$=0.990).

Example 3

Solid Emulsion Gels and Their Affinity to Water

To investigate the affinity of the biphasic systems disclosed herein towards aqueous solvents, a series of deswelling experiments were performed with the gel samples obtained from Example 2. In the deswelling experiments, emulsion gel samples from Example 2 were transferred into 50 mL test tubes and immersed in solutions of PEG 20,000 having the following polymer concentrations: 0.25%, 0.50%, 1.00%, 5.00%, 10.00%, 15.00%, and 20.00%. This resulted in dehydration of the samples. The samples were incubated under moderate agitation for 24 hours at room temperature. The size of the samples was subsequently measured.

The ratio between the initial diameter and the final diameter of the samples at equilibrium with PEG solution was used to calculate the final content of the oil phase. The composition of the samples at equilibrium was then recalculated taking into account the changes in the water content due to osmotic dehydration of the samples in the PEG solution. Data were analyzed in terms of $Q_{FIN}/Q_0$ versus osmotic pressure, where the variables $Q_{FIN}$ and $Q_0$ refer to the final content and the initial content of the oil phase as described in Example 2.

At equilibrium, the swelling pressure of the emulsion gel material was believed to be equal to the osmotic pressure created by the PEG macromolecules. The osmotic pressure of the PEG solution was calculated as reported in Stubbe, B. G. et al. (2002), *Macromolecules*, 35: 2501-2505.

Figure 6:
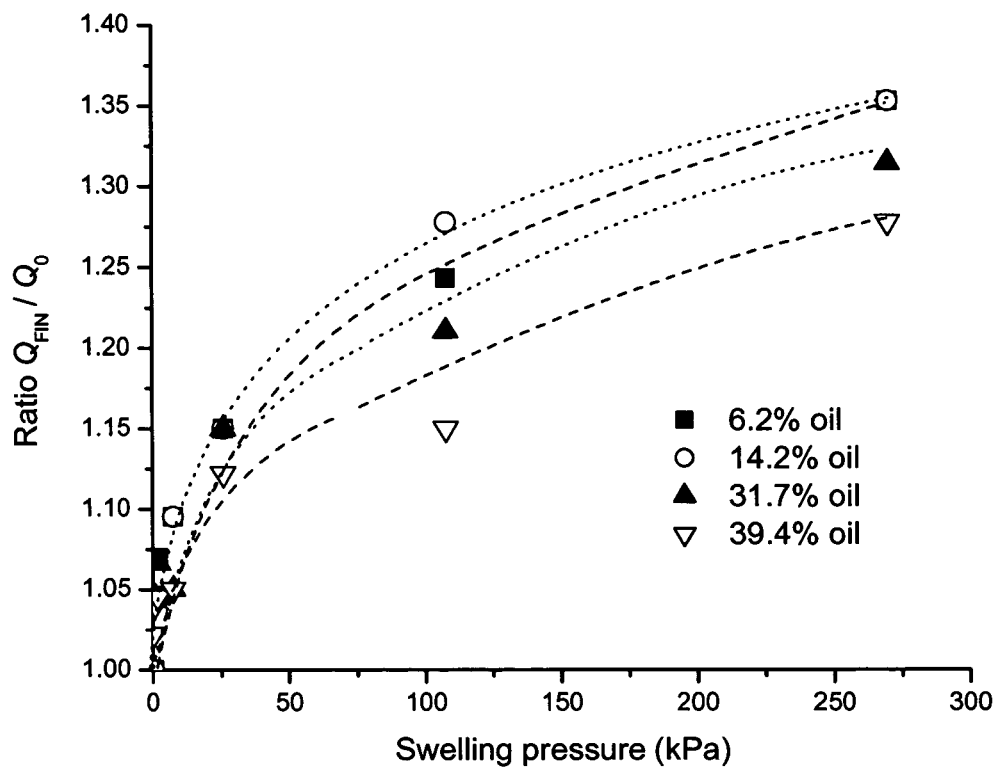
FIG. 6 is a graphical representation of the correlation between the ratio of the equilibrium oil content, $Q_{FIN}$, to the initial oil content, $Q_0$, of certain embodiments of an emulsion gel according to the present teachings and the osmotic pressure created by the polymers in an aqueous solution of PEG-20,000 in which the emulsion gels are incubated.

The ratio between the equilibrium (final) oil content and the initial oil content is shown in FIG. 6 as a function of osmotic pressure. Generally, higher osmotic pressure seemed to have caused more complete dehydration of the material, which manifests itself in an increase of the ratio $Q_{FIN}/Q_0$. The initial oil content also influences the deswelling behavior of the emulsion gel systems. It was observed that water loss is much more pronounced in samples containing a lower oil content (see e.g., data in FIG. 6 related to samples containing 6.2 vol. % and 14.2 vol. % of oil).

Figure 7:
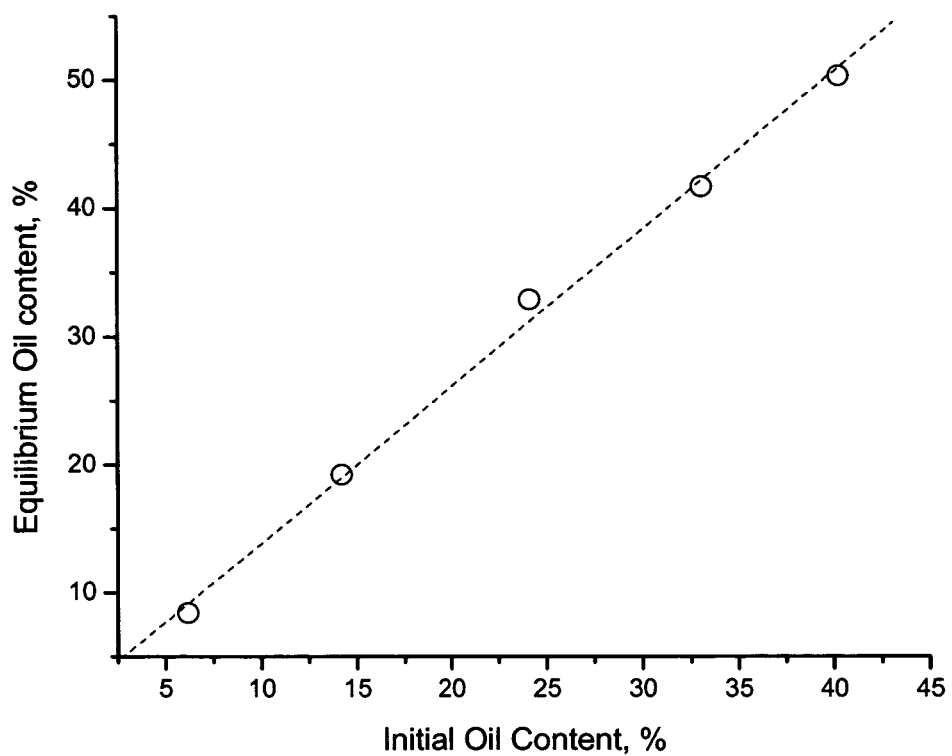
FIG. 7 is a graphical representation of the correlation between the oil content in certain embodiments of an emulsion gel according to the present teachings when the emulsion gels were fully swollen (at equilibrium) and subsequently dehydrated (initial).

Similar to the swelling behavior demonstrated in Example 2, the deswelling behavior of the emulsion gel also appeared to be predictable. Specifically, a linear correlation was observed between the oil content in the samples when they were fully swollen (equilibrium) and subsequently dehydrated (initial). FIG. 7 illustrates the correlation.

Example 4

Diffusion in the Oil Phase

Round-cut pieces of emulsion gel samples containing 25% of oil phase were put in contact with omega-3 oil. The omega-3 oil had been colored with a red pepper pigment. The samples surrounded by the oil were incubated in a 6-well plate for 24 hours. It is known that the red pepper pigment is completely insoluble in water and, therefore, cannot freely diffuse in the aqueous phase of the material.

Transport of the oil was monitored by observing the migration of the red coloration from the pigment. An approximately 3-mm diffusion of the pigment was achieved in the samples exposed to the air after 24 hours of incubation at room temperature. No diffusion of oil was observed when the samples were covered with an impermeable membrane.

This diffusion behavior suggests that individual droplets composing the oil phase of the emulsion gel are interconnected to some degree. As such, a pathway is provided for the relatively rapid diffusion of oil-soluble solutes. Interactions between individual oil droplets become more pronounced when emulsion gels start loosing water. Evaporation of water leads to sudden changes in the material composition and increases the relative volume of the oil phase in the system, which in turn is accompanied by coalescence of the oil droplets.

Example 5

Wound Healing Effect of Omega-3 Oil-Containing Wound Dressings

To study the wound healing effect of omega-3 oil-containing wound dressings, animal studies were conducted with wound dressings of the present teachings and comparative dressings.

Ten pigs weighing 10 to 15 kg were conditioned for at least 2-3 days prior to the study. A commercial growing diet was fed to the pigs and the pigs were housed individually in a temperature-controlled environment (20° C.-25° C.). On Day 0, skin on both sides of the animals was washed with a non-antibacterial soap. Antiseptics were not used because of their potential effects on the healing process. On the back of each pig, four full-thickness wounds (extending to the muscular fascia) were created using a biopsy punch having a diameter of 25 mm.

Before surgery and each subsequent dressing change, animals were anesthetized with a mixture of azaperone and ketamine and maintained under general anaesthesia using isoflurane. Immediately following surgery, each wound was treated with either an omega-3 oil-containing wound dressing ("ω-3 wound dressing") or a comparative dressing that contains olive oil instead of omega-3 oil ("olive oil wound dressing"). The ω-3 wound dressings were prepared according to the procedures described in Example 1. In particular, the volume ratio of the protein solution to omega-3 oil was 1.0:2.0. Omega-3 oil under the trade name NutraSea 'hp' High Potency™ available from Ascenta Health Ltd. (Dartmouth, Nova Scotia, Canada) was used as is. The olive oil wound dressings were similarly prepared using virgin olive oil purchased from a chain grocery store. Each wound dressing was applied under occlusive conditions and renewed every 48 hours.

The wound healing effect of the ω-3 wound dressings was characterized and compared to the olive oil wound dressings by (a) macroscopic determination of wound closure, (b) bacterial count on the wound bed, and (c) histological examination of healing tissues. Wound sites also were visually inspected for signs of edema, erythema, as well as the presence/absence of scar formation.

A. Macroscopic Determination of Wound Closure

The length and width of each wound were measured every two days and the surface area was determined accordingly. The rate of wound closure was determined by the reduction in wound size with the help of planimetry and digital photography. On Day 0 (the day on which the wounds were created), the surface area of each wound was determined and the wound size was considered to be at 100% (i.e., an open wound). A value of 0% represents that the wound had completely closed.

FIG. 8 presents representative photographs of a first wound treated with ω-3 wound dressings and a second wound treated with olive oil wound dressings, as they had healed, respectively, on Day 10, Day 16, and Day 20, of a 30-day study period. The black circle shows the size of the initial wound.

Referring to FIG. 8, wounds treated with ω-3 wound dressings healed very well. For example, it was observed that, although erythema of very light intensity was present during the first ten days, the redness subsided and was no longer observed after Day 11, suggesting that the ω-3 wound dressings have anti-inflammatory properties. In addition, there was only some very slight edema throughout the study period. As can be seen from the specific wound shown, the coloration of the wound approximated that of the surrounding skin by Day 16. Importantly, wounds treated with ω-3 wound dressings also were able to heal without leaving a scar.

In comparison, wounds treated with olive oil wound dressings healed much slower. Edema of light intensity was present throughout the study period. In addition, mild erythema was observed on and off (on Days 2, 6, 12, and 18) throughout the study period, suggesting that the olive oil wound dressings do not seem to have any specific effect on modulating or reducing inflammation. In addition, these wounds, after closure, left visible scars. For example, for the specific wound shown in FIG. 8, there were visible signs of infection (e.g., pus in the middle), and on Day 16, the wound was still very conspicuous in terms of size and coloration.

Table 3 compares the rate of wound size reduction as treated by the two types of dressings. Data in Table 3 are average values that represent the relative size of the wound on a given day as compared to the initial wound size expressed in percentage. As the data indicate, by Day 10, the wounds treated with the ω-3 wound dressings were more than two times smaller than the wounds treated with the olive oil wound dressings. The difference in the wound closure rate related to the two different treatments became even more pronounced after Day 10.

TABLE 3

Relative wound size (expressed in percentage as compared to the initial wound size) after treatment with ω-3 wound dressings and olive oil wound dressings. The values are mean values (n = 20).

| Day | ω-3 wound dressings | Olive oil wound dressings |
| --- | --- | --- |
| 10 | 8.26 ± 1.51 | 19.69 ± 4.40 |
| 12 | 3.53 ± 2.32 | 11.68 ± 4.96 |
| 14 | 1.04 ± 0.48 | 4.71 ± 3.08 |
| 16 | 0.24 ± 0.34 | 3.30 ± 1.60 |

Figure 9:
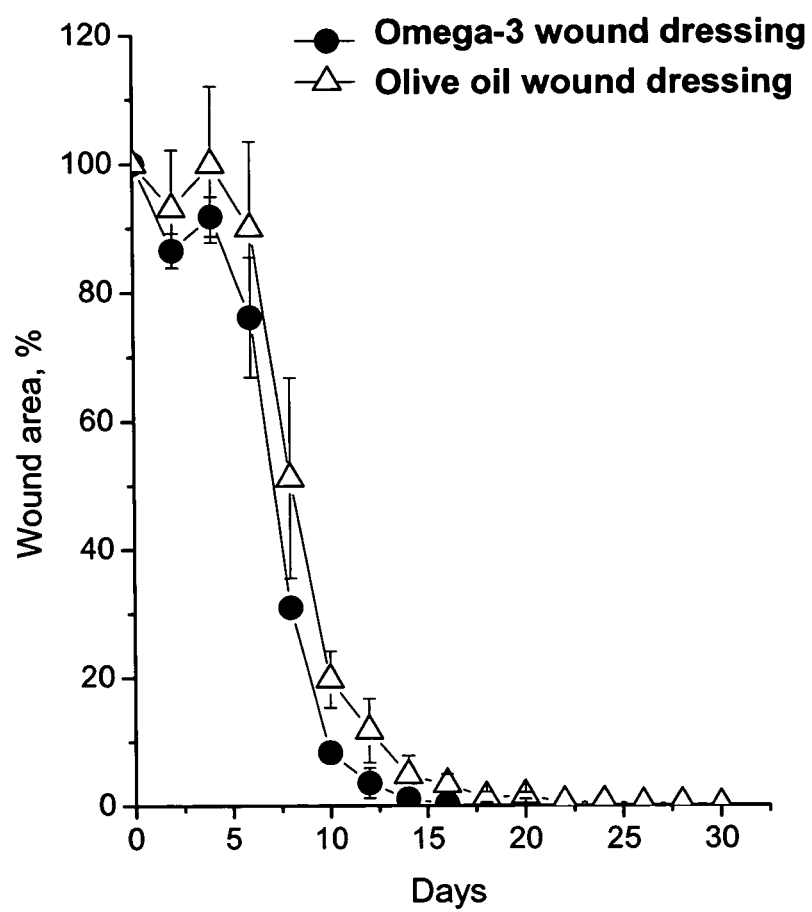
FIG. 9 is a graphical representation of the average rate of wound closure for two groups of wounds (a first group treated with wound dressings of the present teachings and a second group treated with comparative dressings). Values represent the relative surface area of a wound expressed in percentage at a given time point as compared to the initial size of the wound.

FIG. 9 presents the same wound size data graphically and for the entire study period (Day 0 to Day 30). As shown, complete wound closure was achieved by treatment with the ω-3 wound dressings after 18 days. The rate of wound closure was the fastest between Day 5 and Day 10. On Day 5, wounds treated with ω-3 wound dressings had closed only 10% on average (i.e., the average size of these wounds had been reduced to 90% of the size of the initial wounds), whereas on Day 10, wounds treated with ω-3 wound dressings had re-epithelialized on average about 90% (i.e., the average size of these wounds had been reduced to 10% of the size of the initial wounds).

With continued reference to FIG. 9, wounds treated with olive oil wound dressings remained open (wounds were only closed between 5 and 10%) for the first 7 days. Even by Day 20, the average wound still had not closed completely. Accordingly, olive oil does not seem to be an effective agent for promoting wound healing.

Figure 10:
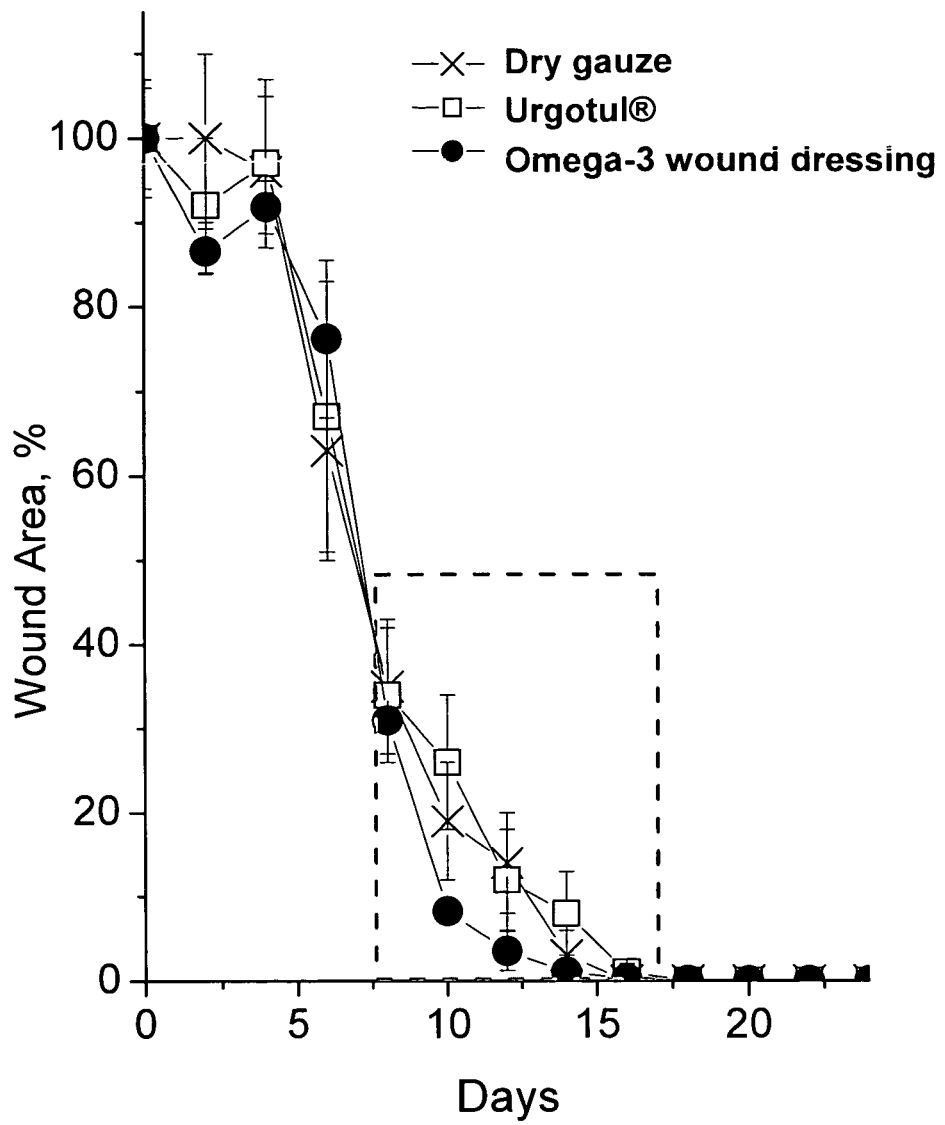
FIG. 10 is a graphical representation of the average rate of wound closure for 20 full-thickness wounds treated with wound dressings of the present teachings, as compared to results obtained from a similar study using dry gauze and a commercially available wound dressing. Values represent the relative surface area of a wound expressed in percentage at a given time point as compared to the initial size of the wound.

FIG. 10 compares treatment by ω-3 wound dressings with treatment by two other wound dressings. Specifically, the data related to ω-3 wound dressings presented in FIG. 9 above were replicated in FIG. 10. The comparison data were drawn from a previous study in publication as Shingel, K. I. et al. (in press), Inflammatory inert poly (ethylene glycol)-protein wound dressing improves healing responses in partial- and full-thickness wounds, INT. WOUND J., in which full-thickness wounds were treated with dry gauze and Urgotul® dressing (Laboratoires Urgo, Chenôve, France), respectively, using similar procedures.

As shown in FIG. 10, the wound closure rate in connection with treatment by ω-3 wound dressings was significantly faster than the wound closure rate in connection with treatment by dry gauze or treatment by the Urgotul® dressing. The data demonstrate that the ω-3 wound dressings are very effective in promoting wound healing, especially when compared to the three comparative dressings studied in this example.

B. Bacterial Count on the Wound Bed

Samples of normal skin flora were taken before Day 0, on which the full-thickness wounds were created. A sterile cylinder having a diameter of 2.5 cm was tightly pressed against the pre-shaven (but unwashed) skin on the back of the pigs. Phosphate buffer (10 mL) was pipetted into the cylinder and was mechanically mixed. The fluid was agitated for 1 minute (at a speed sufficient to produce a vortex), then removed with a sterile pipette and transferred to a test tube.

Additional microbial flora samples were collected from each wound at predetermined time points during the 30-day study period, and after euthanasia of the pigs, using identical techniques.

Using these samples, microbiological analyses were conducted to (i) identify microbial species found in normal skin flora versus wound flora, (ii) note the presence of specific microbial species (including Staphylococcus aureus, beta-hemolytic streptococci (e.g., S. pyogenes, S. agalactiae), non-fermenters, and Enterobacteriaceae), and (iii) compare the antibacterial potency of ω-3 wound dressings versus olive oil wound dressings.

Figure 11:
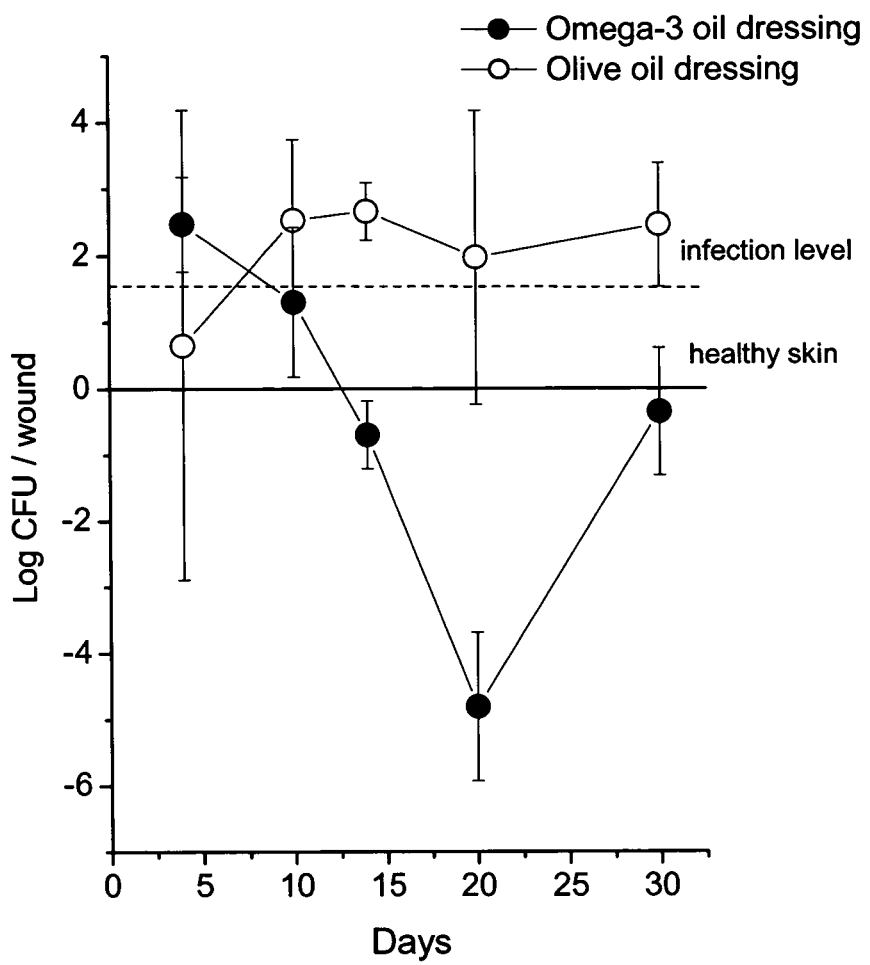
FIG. 11 is a graphical representation of the microbial load found in full-thickness wounds treated with wound dressings according to the present teachings and full-thickness wounds treated with comparative dressings, as compared to healthy skin cultures.

FIG. 11 shows the bacterial load found on healthy skin compared to wounds treated with ω-3 wound dressings and wounds treated with olive oil wound dressings, respectively. As shown in FIG. 11, wounds treated with ω-3 wound dressings showed a significant reduction in the bacterial load between Day 4 and Day 20 during the 30-day study period. This decrease goes well below the healthy skin level. Although an increase in bacterial load was observed between Day 20 and Day 30, the bacterial load on Day 30 was still lower than the healthy skin level. In summary, it was observed that treatment with ω-3 wound dressings had led to a reduction of bacterial load in the wound bed.

By comparison and with continued reference to FIG. 11, wounds treated with olive oil wound dressings showed a higher bacterial content relative to healthy skin cultures, and a general increase in bactierial load was observed throughout the study period. It can be seen from FIG. 11 that the bacterial load for these wounds was always higher than the healthy skin level. More importantly, after Day 10, the bacterial load was sufficiently high to pose a risk of infection.

Specific microbial species were identified and quantified in a second part of this study. The following observations were made: (a) Staphylococcus aureus was isolated in 80% of the healthy skin cultures and in 100% of the cultures obtained from wounds treated with ω-3 wound dressings and from wounds treated with olive oil wound dressings; (b) pathogenic streptococci were found in 100% of the healthy skin cultures, but only in 40% of the cultures obtained from wounds treated with ω-3 wound dressings and in 60% of the cultures obtained from wounds treated with olive oil wound dressings; (c) non-fermenters were found in 100% of the healthy skin cultures and in none of the cultures obtained from wounds treated with ω-3 wound dressings and from wounds treated with olive oil wound dressings; and (d) enterobacteriaceae were found in equal frequencies in healthy skin cultures and in wound cultures.

Together, these data demonstrate that the ω-3 wound dressings appear to have at least some antibacterial effect, which helps to reduce the risk of infection, and lead to faster and more efficient wound healing.

C. Histological Examination of Healing Tissues

Tissue samples were obtained after pigs were euthanized at predetermined time points by an overdose of sodium pentobarbital. Immediately following the sacrifice of the animals, the skin on the back of each pig was removed and fixed in 10% neutral buffered formalin. After at least 24 hours, but less than 96 hours, the fixed tissues were prepared for paraffin embedding. The wounded sections of the skin were visually identified and a midline as well as a perpendicular incision of this skin section were made. The skin samples were then embedded in paraffin, blocks were sectioned at 5 μm, and the following stains were performed: hematoxylin/eosin for general observation, Masson's Trichrome for collagen organization and Red Oil for observation of diffusion of the lipids (omega-3 oil and olive oil).

Histological examination of the healing tissues revealed that all of the studied wounds, whether treated with ω-3 wound dressings or olive oil wound dressings, were able to heal without acute inflammation, edema, or erythema. However, different patterns of collagen formation and deposition were observed with respect to the different treatments, in particular, at the beginning of the wound healing process as a result of varied fibroblast activity.

More specifically, for wounds treated with ω-3 wound dressings, collagen deposits in the wound bed could be observed as early as four days post injury. By Day 30, it was observed that collagen deposits had formed a mature structure and were organized parallel to the skin surface.

Figure 12:
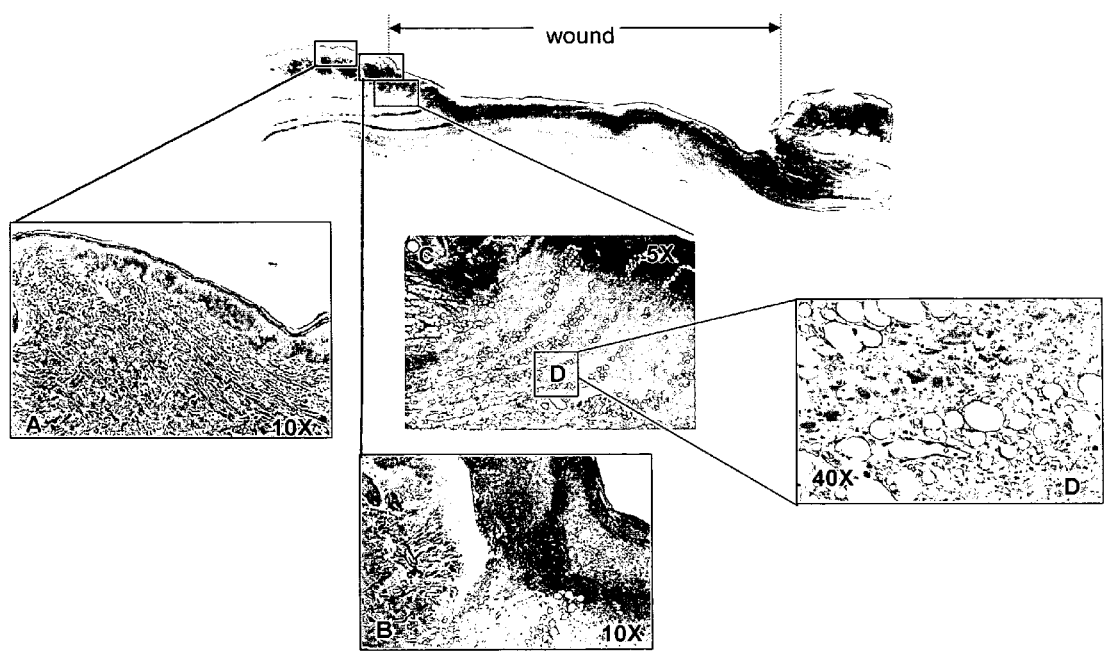
FIG. 12 is a color histological photograph of a full-thickness wound treated with wound dressings according to the present teachings four days after the initial injury.

FIG. 12 is a color histological photograph of a full-thickness wound treated with ω-3 wound dressings 4 days after the initial injury. The area A shows that healthy skin surrounding the wound has a small amount of inflammatory infiltrates. The area marked as B shows granulation tissues. The area C shows moderate fibroblast activity in the newly formed dermis. In area D, it is possible to observe an organized diffusion pattern of lipid droplets through the epidermis and the dermis. The special coloration associated with the Red Oil stain confirmed the exogenous origin of these lipid deposits.

Figure 13:
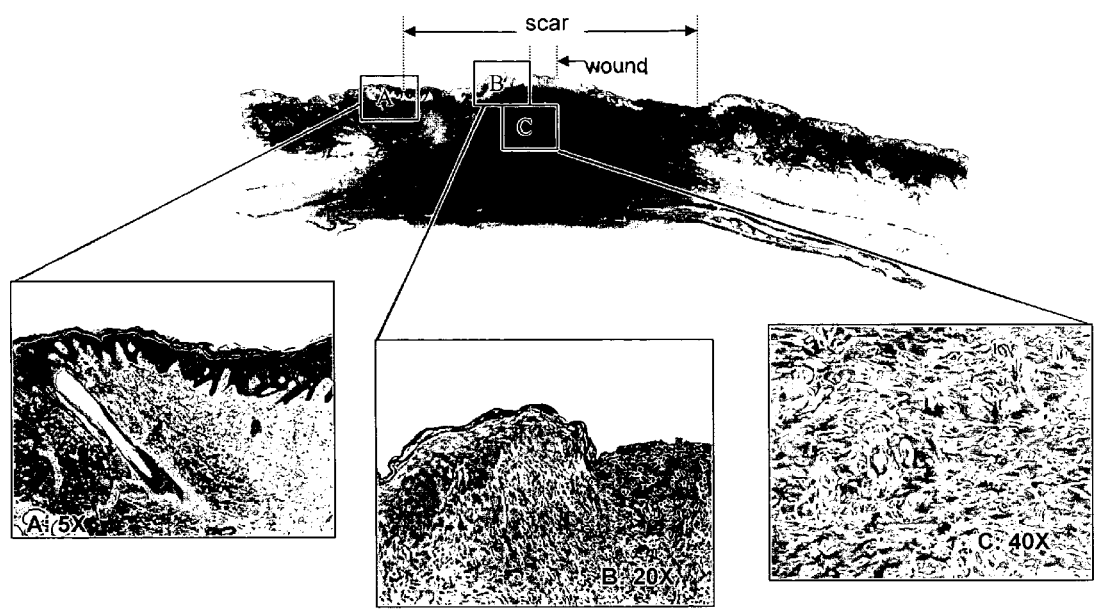
FIG. 13 is a color histological photograph of a full-thickness wound treated with wound dressings according to the present teachings ten days after the initial injury.

Referring to FIG. 13, which shows a color histological photograph of a similar full-thickness wound treated by ω-3 wound dressings 10 days after the initial injury, it can be seen that the neo-epidermis (area B) was well-stratified and keratinized. In the healthy skin surrounding the wound (area A), only a moderate amount of inflammatory infiltrates was observed to be present. Area C shows pronounced fibroblast activity in the new dermis accompanied by pronounced collagen formation and deposition.

Figure 14:
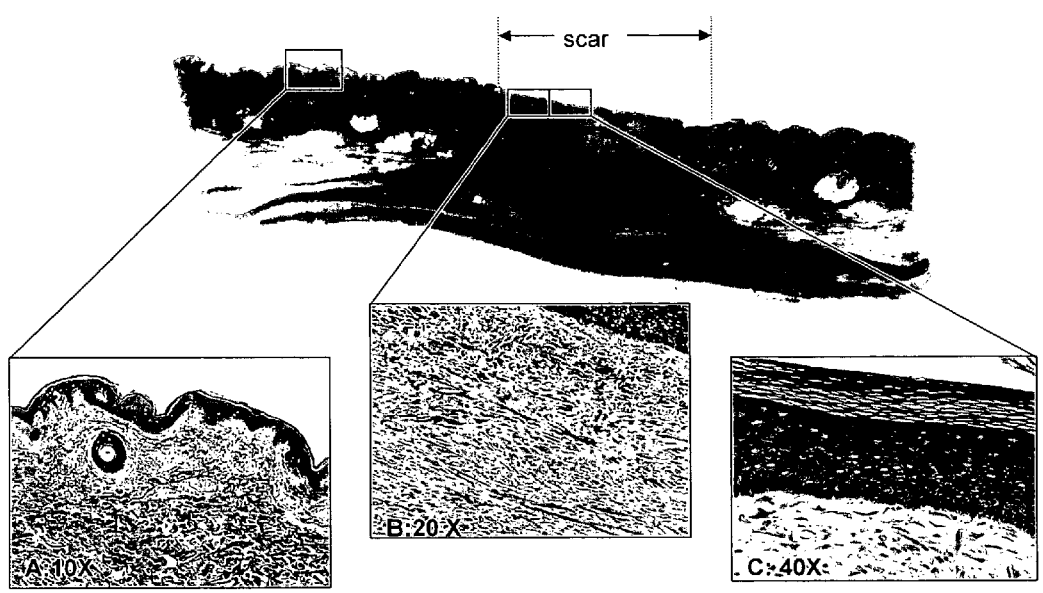
FIG. 14 is a color histological photograph of a full-thickness wound treated with wound dressings according to the present teachings thirty days after the initial injury.

FIG. 14 shows a color histological photograph of a similar full-thickness wound treated by ω-3 wound dressings 30 days after the initial injury. The area A shows newly formed dermis around the wound skin where a small amount of inflammatory infiltrates can be observed to be present. Area C shows well-stratified and keratinized neo-epidermis. Most notably, the collagen deposits in area B can be seen to be well-organized parallel to the skin surface.

Without wishing to be bound to any particular theory, it is believed that the omega-3 oil-containing wound dressings of the present teachings are able to accelerate wound healing without forming a scar because the wound dressings disclosed herein are capable of effectively delivering omega-3 oil to the wound bed, and the omega-3 oil so delivered is able to modulate dermal regeneration (e.g., without overstimulation of tissue regeneration) and prevent uncontrolled contraction of the wound. Without wishing to be bound to any particular theory, it is further believed that the omega-3 rich lipid droplets can be coupled to newly formed blood vessels and fibroblasts, triggering angiogenesis as well as fibroblasts proliferation.

The data presented in this example demonstrate that the ω-3 wound dressings disclosed herein can have antibacterial and anti-inflammatory properties, and can effectively accelerate wound healing while preventing scar formation.

Variations, modifications, and other implementations of what is described herein will occur to those of ordinary skill in the art without departing from the spirit and the essential characteristics of the present teachings. Accordingly, the scope of the present teachings is to be defined not by the preceding illustrative description but instead by the following claims, and all changes that come within the meaning and range of equivalency of the claims are intended to be embraced therein.

Each of the patent documents and scientific publications disclosed hereinabove is incorporated by reference herein for all purposes.

What is claimed is:

1. A solid or semi-solid gel comprising:
a hydrogel matrix; and
a hydrophobic oil dispersed within the hydrogel matrix;
wherein the hydrogel matrix comprises water and a protein covalently crosslinked by a hydrophilic, gel-forming polymer comprising polyethylene glycol, and wherein said gel is adapted for inclusion in a drug delivery system and/or inclusion in a wound dressing that is applied to an external surface of a subject.

2. The solid or semi-solid gel of claim 1, wherein the gel is water-insoluble.

3. The solid or semi-solid gel of claim 1, wherein the gel has a predetermined shape and size.

4. The solid or semi-solid gel of claim 1, wherein the protein has antioxidant properties.

5. The solid or semi-solid gel of claim 1, wherein the protein is selected from the group consisting of bovine serum albumin, human serum albumin, lactalbumin, ovalbumin, soy albumin, pea albumin, hydrolyzed soy protein, hydrolyzed wheat protein, casein, and mixtures thereof.

6. The solid or semi-solid gel of claim 1, wherein the hydrophobic oil is a natural oil selected from an animal oil, a vegetable oil, a mineral oil, and mixtures thereof.

7. The solid or semi-solid gel of claim 1, wherein the hydrophobic oil is an omega-3 oil.

8. The solid or semi-solid gel of claim 1, wherein the hydrophobic oil comprises an oil comprising one or more of alpha-linolenic acid, eicosapentaenoic acid, and docosahexaenoic acid.

9. The solid or semi-solid gel of claim 1, wherein the hydrophobic oil further comprises a biologically active agent.

10. A drug delivery device comprising the solid or semi-solid gel of claim 1 and a biologically active agent.

11. The solid or semi-solid gel of claim 1, wherein content of the hydrophobic oil is in the range of about 9-50% w/w, and wherein water content of the gel is in the range of about 41-83 w/w.

12. A solid or semi-solid gel comprising:
a hydrogel matrix comprising water and hydrolyzed soy protein covalently crosslinked by polyethylene glycol; and
a hydrophobic oil comprising an omega-3 oil dispersed within the hydrogel matrix; wherein said solid or semi-solid gel is adapted for inclusion in a drug delivery system and/or inclusion in a wound dressing that is applied to an external surface of a subject.

13. A drug delivery device for an external surface of a subject comprising a hydrogel matrix having dispersed therein a hydrophobic oil and a biologically active agent, wherein the hydrogel matrix comprises water and a protein covalently crosslinked by a hydrophilic, gel-forming polymer comprising polyethylene glycol; and wherein said drug delivery device provides concomitant transdermal delivery of hydrophilic and hydrophobic compounds.

14. A wound dressing comprising a backing and the solid or semi-solid gel of claim 1.

15. The wound dressing of claim 14, wherein the hydrophobic oil comprises an omega-3 oil.

16. The wound dressing of claim 15, wherein the hydrophobic oil further comprises one or more of alpha-linolenic acid, eicosapentaenoic acid, and docosahexaenoic acid.

17. The wound dressing of claim 15, wherein the backing comprises at least one of a polymeric film and a fabric layer.

18. The wound dressing of claim 17, wherein the omega-3 oil is incorporated into the polymeric film or impregnated within the fabric layer.

19. A method for treating a wound, the method comprising applying to a wound the solid or semi-solid gel of claim 1.

20. The method of claim 19, wherein the wound is selected from the group consisting of a burn wound, an acute wound, a chronic wound, a necrotic wound, and a laceration.

21. The method of claim 19, wherein said hydrogel matrix comprises water and hydrolyzed soy protein covalently crosslinked by polyethylene glycol; wherein the hydrophobic oil is an omega-3 oil dispersed within the hydrogel matrix; and wherein said solid or semi-solid gel is incorporated in a wound dressing.

22. A method for preparing a solid or semi-solid gel according to claim 1, the method comprising:
dispersing an hydrophobic oil in an aqueous protein solution to form an oil-in-water emulsion; and
a hydrophilic, gel-forming polymer comprising polyethylene glycol to the emulsion, wherein the polymer covalently crosslinks the protein in the oil-in-water emulsion to form a hydrogel matrix, thereby preparing a solid or semi-solid emulsion gel comprising a hydrogel matrix and a hydrophobic oil dispersed therein.

23. The method of claim 22, comprising dissolving a biologically active agent in the oil before forming the oil-in-water emulsion.

* * * * *